(12) United States Patent
Wang

(10) Patent No.: US 8,457,380 B2
(45) Date of Patent: Jun. 4, 2013

(54) PET LOCAL TOMOGRAPHY

(75) Inventor: Wenli Wang, Aurora, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 679 days.

(21) Appl. No.: 12/600,666

(22) PCT Filed: May 6, 2008

(86) PCT No.: PCT/IB2008/051764
§ 371 (c)(1), (2), (4) Date: Mar. 17, 2010

(87) PCT Pub. No.: WO2008/146186
PCT Pub. Date: Dec. 4, 2008

(65) Prior Publication Data
US 2010/0303319 A1    Dec. 2, 2010

Related U.S. Application Data

(60) Provisional application No. 60/940,722, filed on May 30, 2007.

(51) Int. Cl.
*G06K 9/00* (2006.01)

(52) U.S. Cl.
USPC ........................................ 382/131

(58) Field of Classification Search
USPC ........................................ 382/131
See application file for complete search history.

(56) References Cited

U.S. PATENT DOCUMENTS

| | | | |
|---|---|---|---|
| 5,539,800 A | | 7/1996 | Katsevich et al. |
| 5,550,892 A | | 8/1996 | Katsevich et al. |
| 5,717,211 A | | 2/1998 | Katsevich |
| 5,953,388 A | | 9/1999 | Walnut et al. |
| 6,147,353 A | * | 11/2000 | Gagnon et al. .......... 250/363.05 |
| 6,385,286 B1 | | 5/2002 | Fitchard et al. |
| 6,473,634 B1 | * | 10/2002 | Barni ............................ 600/425 |
| 2003/0161443 A1 | * | 8/2003 | Xiao et al. ..................... 378/210 |
| 2004/0066911 A1 | | 4/2004 | Hsieh et al. |
| 2005/0249432 A1 | * | 11/2005 | Zou et al. ...................... 382/276 |
| 2006/0140482 A1 | | 6/2006 | Koehler |
| 2006/0284095 A1 | | 12/2006 | Muehllehner et al. |
| 2007/0010731 A1 | | 1/2007 | Mistretta |

(Continued)

FOREIGN PATENT DOCUMENTS

| | | |
|---|---|---|
| GB | 2164230 A | 3/1986 |
| WO | 2006109203 A1 | 10/2006 |
| WO | 2007054843 A1 | 5/2007 |

OTHER PUBLICATIONS

Shepp, et al., Maximum Likelihood Reconstruction for Emission Tomography , IEEE Trans. Med. Imaging, 1982, pp. 113-122, vol. MI-2.

(Continued)

*Primary Examiner* — Gerlad J. O'Connor
*Assistant Examiner* — Trang Nguyen

(57) ABSTRACT

A positron imaging apparatus (102) acquires projection data indicative of positron annihilations in an object under examination. A local reconstructor (146) performs an iterative local reconstruction of truncated projection data to produce image space data indicative of the object. A motion compensator (142) compensates for a motion of the object; an image combiner (148) combines the image space data with other image space data indicative of the object.

19 Claims, 5 Drawing Sheets

U.S. PATENT DOCUMENTS

| | | | |
|---|---|---|---|
| 2007/0040122 | A1 | 2/2007 | Manjeshwar et al. |
| 2007/0076933 | A1 | 4/2007 | Starman et al. |
| 2008/0056550 | A1* | 3/2008 | Kadir et al. .................. 382/131 |
| 2008/0099686 | A1* | 5/2008 | Defrise et al. ........... 250/363.04 |
| 2008/0240335 | A1* | 10/2008 | Manjeshwar et al. ............. 378/4 |
| 2010/0166274 | A1* | 7/2010 | Busch et al. .................. 382/131 |

OTHER PUBLICATIONS

Hudson et al, Accelerated Image Reconstruction Using Ordered Subsets of Projection Data, IEEE Transactions on Medical Imaging, 1994, p. 601-609, vol. 13, No. 4.

Spyra, et al., Computed Tomographic Imaging of the Coronary Arterial Tree-Use of Local Tomography, IEEE Transactions on Medical Imaging, Mar. 1990, pp. 1-4, vol. 9, No. 1.

Olson, et al., Wavelet Localization of the Radon Transform, IEEE Transactions on Signal Processing, Aug. 1994, pp. 2055-2067, vol. 42, No. 8.

Mumcuoglu, et al., Fast Gadient-Based Methods for Bayesian Reconstruction of Transmission and Emission PET Images, IEEE Transactions on Medical Imaging, Dec. 1994, pp. 687-701, vol. 13, No. 4.

Byrne, Acceleration the EMML Algorithm and Related Iterative Algorithms by Rescaled Block-Iterative Methods, IEEE Transaction on Image Processing, 1998, pp. 100-109, vol. 7, No. 1.

Brown et al., A Row-Action Alternative to the EM Algorithm for Maximizing Likelihoods in Emission Tomography, IEEE Transactions on Medical Imaging, 1996, p. 687-699, vol. 15, No. 5.

Ramm, et al., THe Radon Transform and Local Tomography, CRC Press, 1996.

Zeng, et al., Single Photon Emission Local Tomography (SPELT), 1996 IEEE Nuclear Science Symposium, Nov. 2-9, 1996, pp. 1Zeng, et al, Single Photon Emission Local Tomography (SPELT), 1996 IEEE Nuclear Science Symposium, Nov. 2-9, 1996, pp. 1628-1632, vol. 3.628-1632, vol. 3.

Holschneider, Inverse Radon Transforms Through Inverse Wavelet Transforms, Inverse Problems, 1999, pp. 853-861, vol. 7.

Goldstein, et al., Limited-Memory Quasi-Newton Iterative Reconstruction in Emission Computed Tomography, Journal of Nuclear Medicine, May 1999, p. 74P, vol. 40, http://clio.rad.sunysb.edu/pub/PAPERS/snm991.pdf.

Zeng, et al., Local Tomography Property of Residual Minimization Reconstruction With Planar Integral Data, IEEE Transactions on Nuclear Science, Oct. 2003, pp., 1590-1594, vol. 50, No. 5.

Bardsley, J. M.; A Limited-Memory, Quasi-Newton Preconditioner for Nonnegatively Constrained Image Reconstruction, Jose A, pp. 724-731, vol. 21, issue 5, 2004.

Bilgot, et al., Wavelets, Local Tomography and Interventional X-Ray Imaging, 2004 IEEE Nuclear Science Symposium Conference Record, Oct. 16-22, 2004, pp. 3505-3509, vol. 6.

Conti, et al., First Experimental Results of Time-of-Flight Reconstruction on an LSO PET Scanner, Physics in Medicine and Biology, 2005, pp. 4507-4526, vol. 50, Institute of Physics Publishing.

Defrise, et al., Fourier Rebinning of Time-of-Flight PET Data, Physics in Medicine and Biology, Jun. 21, 2005, pp. 2749-2763, vol. 50.

Charles C. Watson, An Evaluation of Image Noise Variance for Time-of-Flight PET, IEEE Nuclear Science Symposium Conference Record 2005, Oct. 23-29, 2005, pp. 2041-2045, vol. 4.

Surti, et al.; Investigation of Time-of-Flight Benefit for Fully 3-D PET; 2006; IEEE Trans. on Medical Imaging; 25(5) 529-538.

Matej, et al.; Efficient 3D TOF PET Reconstruction Using View-Grouped Histo-Images; 2006; IEEE Trans. on Nuclear Science; vol. 3:1728-1735.

Wang, et al.; Systematic and Distributed Time-of-Flight List Mode PET Reconstruction; 2006; IEEE Trans. on Nuclear Science; vol. 3:1715-1722.

* cited by examiner

PET LOCAL TOMOGRAPHY

CROSS REFERENCE TO RELATED APPLICATIONS

This application claims the benefit of U.S. provisional application Ser. No. 60/940,722 filed May 30, 2007, which is incorporated herein by reference.

The following relates to the field of positron imaging, and more especially to the reconstruction of data acquired in positron emission tomography (PET). It finds particular application to medical and other application where it is desirable to produce image data indicative of a local region of interest of an object under examination.

Positron emission tomography (PET) is a branch of nuclear medicine in which a positron-emitting radiopharmaceutical such as $^{18}$F-fluorodeoxyglucose (FDG) is introduced into the body of a patient. As the radiopharmaceutical decays, positrons are generated. More specifically, each of a plurality of positrons reacts with an electron in what is known as a positron annihilation event, thereby generating a coincident pair of 511 keV gamma rays which travel in opposite directions along a line of response (LOR). A gamma ray pair detected within a coincidence time is ordinarily recorded by the PET scanner as an annihilation event.

Developments in detector technology have led to the availability of flight (TOF) PET scanners, in which the arrival time differences of the coincident gamma ray pairs are also acquired. The TOF information predicts the most likely position of the annihilation along the LOR. As practical detector systems are characterized by a finite timing resolution, the annihilation location is usually modeled according to a Gaussian probability distribution.

It has been recognized that TOF PET improves noise variance more toward the periphery of an object and thus has improved lesion detectability than conventional non-TOF PET for larger objects. It also has the benefit of using less projection angle to provide an image resolution comparable to that of non-TOF PET. It is also less sensitive to detector normalization and imperfect scatter correction than non-TOF PET.

Data from a scan is used to reconstruct volumetric or image space data indicative of the distribution of the radionuclide in the object, typically using iterative reconstruction techniques. Examples of iterative reconstruction techniques include the maximum likelihood expectation maximization (ML-EM), ordered subsets expectation maximization (OS-EM), resealed block iterative expectation maximization (RBI-EM), row action maximization likelihood (RAMLA), conjugate gradient (CG), and limited memory quasi-Newton (LMQN) techniques. See Shepp and Vardi, *Maximum Likelihood Reconstruction for Emission Tomography*, IEEE Trans. Med. Imaging vol. MI-2, pp 113-122 (1982); Hudson and Larkin, *Accelerated Image Reconstruction Using Ordered Subsets of Projection Data*, IEEE Trans. Med. Imaging vol. 13, no. 4, pp 601-609 (1994); Byrne, *Accelerating the EMML Algorithm and Related Iterative Algorithms by Rescaled Block-Iterative Methods*, IEEE Trans. Image Processing, vol. 7, no. 1 pp. 100-109 (1998); Brown and DePierro, *A Row-Action Alternative to the EM Algorithm for Maximizing Likelihoods in Emission Tomography*, IEEE Trans. Med. Imaging vol. 15, no. 5, pp 687-699 (1996); Mumcuoglu, E. U.; Leahy, R.; Cherry, S. R.; Zhenyu Zhou, *Fast gradient-based methods for Bayesian reconstruction of transmission and emission PET images*, IEEE Trans. Med. Imag., 13(4): 687-701 (1994); C. Goldstein, W. Wang and G. Gindi, *Limited-Memory Quasi-Newton Iterative Reconstruction in Emission Computed Tomography*, 46th Annual Meeting of the Society of Nuclear Medicine, California, (1999); J. M. Bardsley, *A limited-memory, quasi-Newton preconditioner for nonnegatively constrained image reconstruction*, J. Opt. Soc. Am. A 21, 724-731 (2004).

Analytical algorithm-based local tomography reconstruction techniques have used truncated projection data of the projection data to reconstruct a local region of interest (ROI) of an object. Filtered back projection (FBP)-based analytical algorithms have been used to find the discontinuity in an ROI for Radon and exponential Radon transforms. See Ramm, et al., *The Radon Transform and Local Tomography* (CRC Press, 1996); Katsevich, et al., U.S. Pat. No. 5,539,800, entitled Pseudolocal Tomography; Katsevich, et al., U.S. Pat. No. 5,550,892, entitled Enhanced Local Tomography; Katsevich, et al., U.S. Pat. No. 5,717,211, entitled Generalized Local Emission Tomography. A wavelet-based analytical approach has also been used in X-ray local tomography. See Walnut, et al., U.S. Pat. No. 5,953,388, entitled Method and Apparatus for Processing Data from Tomographic Imaging Systems; Bilgot, et al., *Wavelets, Local Tomography and Interventional X-Ray Imaging*, IEEE Nuclear Science Symposium 2004 Conference Record, vol. 6, pp. 3505-3509 (October 2004); see also Holschneider, *Inverse Radon Transforms Through Inverse Wavelet Transforms*, Inverse Problems, vol. 7 pp. 853-861 (1999). An iterative conjugate gradient algorithm has also been employed in local ROI reconstruction for planar integral data generated using a rotating strip detector in a single photon emission computed tomography (SPECT) application. See Zeng, et al., *Local Tomography Property of Residual Minimization Reconstruction with Planar Integral Data*, IEEE Transactions on Nuclear Science, vol. 50, no. 5, pp. 1590-1594 (2003). In SPECT, generally speaking, iterative algorithms outperform analytical methods for local tomography.

Aspects of the present application address these matters and others.

According to a first aspect, an apparatus includes a projection data spatial truncator that spatially truncates positron emission projection data acquired in a positron emission examination of an object and an iterative reconstructor that reconstructs the truncated projection data to produce first image space data indicative of the object.

According to another aspect, a positron emission local tomography method includes iteratively reconstructing spatially truncated projection data indicative of positron annihilations occurring in an object and acquired using a positron emission scanner to produce first image space data indicative of the object. The method also includes presenting the first image space data in a human perceptible form.

According to another aspect, a computer readable storage medium contains instructions which, when executed by a computer, cause the computer to carry out a method. The method includes performing an iterative local reconstruction of spatially truncated projection data acquired in a positron emission examination of an object to produce first image space data indicative of the object.

According to another aspect, an apparatus includes a position emission scanner and an iterative local reconstructor in operative communication with the scanner. The reconstructor reconstructs spatially truncated projection data acquired along lines of response that intersect a transverse sub-region of the object to produce first image space data indicative of the object. The apparatus also includes a motion compensator that compensates for a motion of the sub-region.

Those skilled in the art will appreciate still other aspects of the present invention upon reading and understanding the appended description.

The invention may take form in various components and arrangements of components, and in various steps and arrangements of steps. The drawings are only for purposes of illustrating the preferred embodiments and are not to be construed as limiting the invention.

Figure 1:
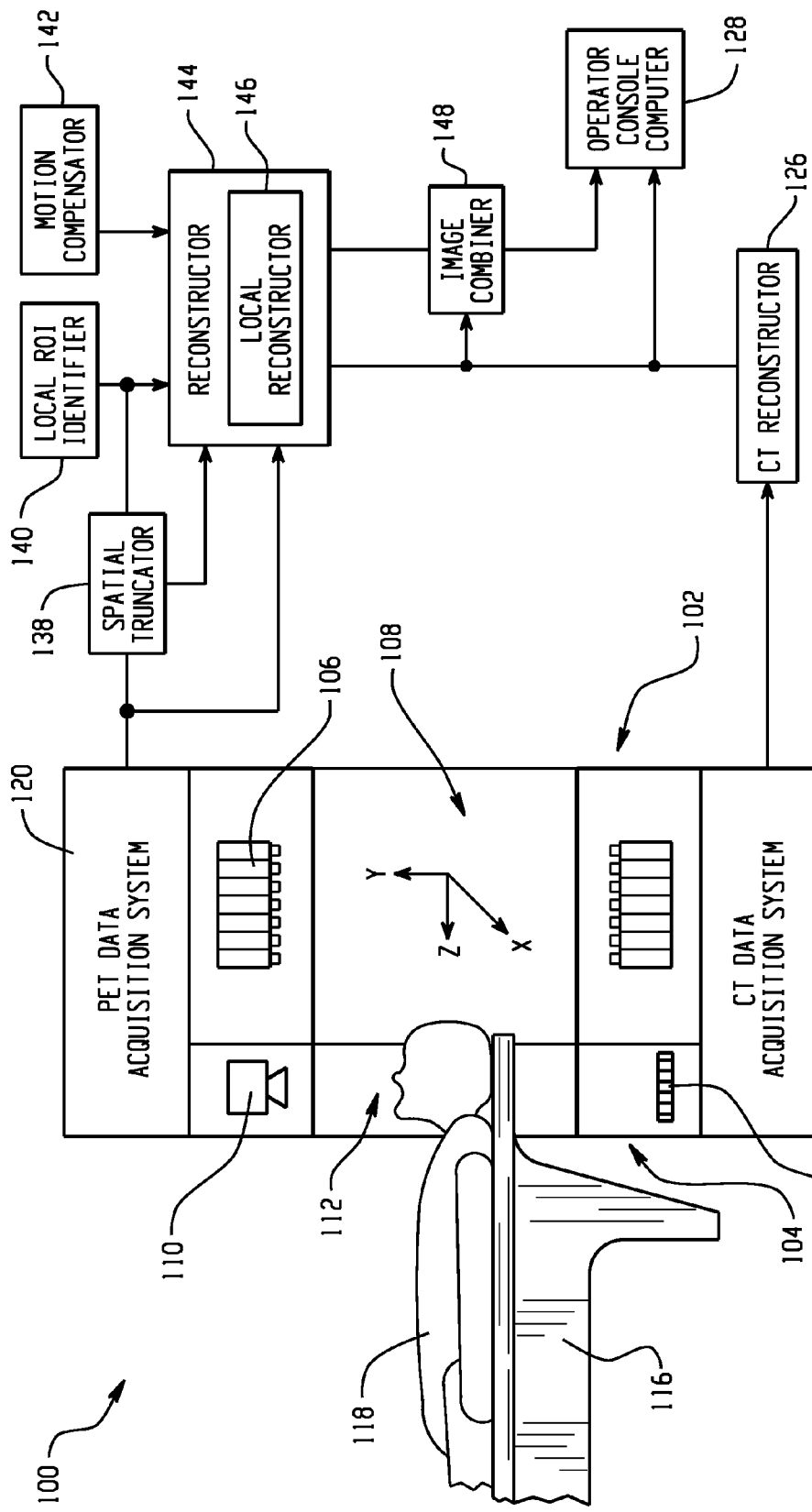
FIG. 1 depicts a combined PET/CT system.

With reference to FIG. 1, a combined PET/CT system 100 includes a PET gantry portion 102 and a CT gantry portion 104. The PET gantry portion 102 includes gamma radiation sensitive detectors 106 disposed in a ring about an examination region 108. The detectors 106 detect gamma radiation characteristic of positron annihilation events occurring within a PET examination region 108. Depending on factors such as the geometry and design of the detector system, the PET system may have an effective transverse field of view (FOV) that is smaller than the transverse dimension of the examination region 108.

The CT portion 104 includes a radiation source 110 such as an x-ray tube that rotates about a CT examination region 112. Radiation sensitive detectors 114 detect radiation emitted by the x-ray source which has traversed the examination region 112. The transverse FOV of the CT portion 104 is a function of factors such as the geometry and design of the x-ray source 110 and detector 114, and may in some cases be smaller or otherwise different than the transverse FOV of the PET portion 102.

The PET gantry portion 102 and CT gantry portion 104 are preferably located in proximity with their respective examination regions 108, 112 disposed along a common longitudinal or z-axis. An object support 116 supports an object to be imaged 118 such as human patient. The object support 116 is preferably longitudinally movable in coordination with operation of the PET/CT system 100 so that the object 118 can be scanned at a plurality of longitudinal locations by both the PET and CT gantry portions 102, 104.

A CT data acquisition system 122 processes the signals from the CT detectors 114 to generate CT projection data indicative of the radiation attenuation along a plurality of lines or rays through the examination region 112. A CT reconstructor 126 reconstructs the CT projection data using suitable reconstruction algorithms to generate image data indicative of the spatially varying radiation attenuation of the object 118.

A PET data acquisition system 120 provides PET projection data such as a list of annihilation events detected by the detectors 106. More particularly, the projection data provides information on the LOR for each event, such as a transverse and longitudinal position of the LOR, its transverse and azimuthal angles, and TOF information in the case of a system having time of flight capabilities. Alternately, the data may be rebinned into one or more sinogram or projection bins.

A local region of interest (ROI) identifier 140 identifies a local ROI that is ordinarily a subset of the larger object under examination. In one technique, the ROI is determined using a priori information about the object. In the case of a human patient, for example, the location of an ROI that includes an organ such as the heart may be estimated using known morphological characteristics. In another implementation, a computer processor identifies a location of the ROI either automatically or semi-automatically in a low resolution or other reconstruction of the CT or PET system data, for example to locate a lesion, a center of activity, or other field of interest. The ROI may also be manually delineated by the user using a low resolution or other image. In still another implementation that is particularly applicable to situations where a portion of the object lies outside the effective transverse FOV of one or both of the PET and/or CT systems, the ROI may be established as that portion of the object located within the relevant field of view. Note that the foregoing techniques may be combined; other suitable techniques may also be used.

Figure 2:
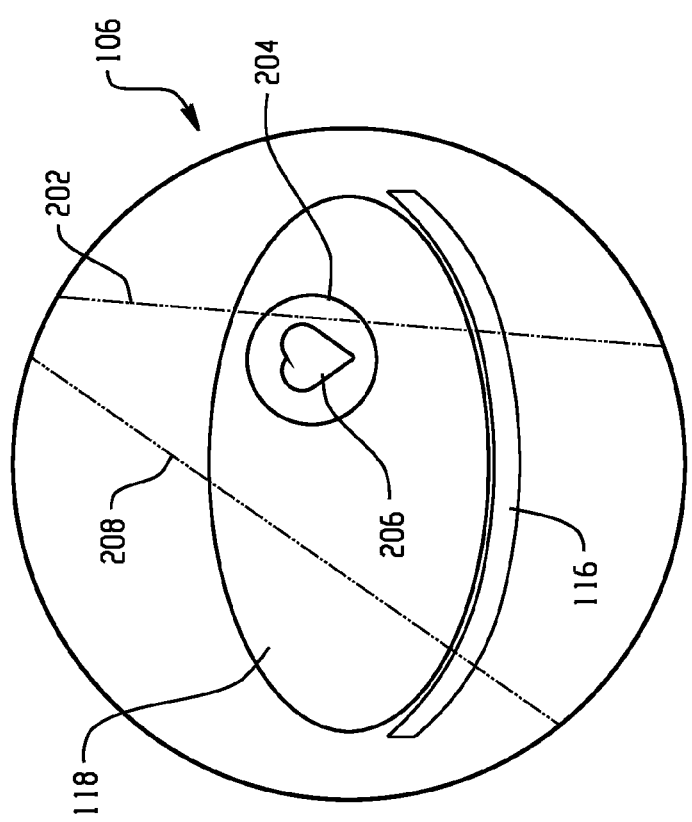
FIG. 2 illustrates an operation of a projection data spatial truncator.

A PET projection data spatial truncator 138 spatially truncates the projection data, for example by identifying projection data acquired along LORs that pass through the identified ROI or rejecting those that do not. By way of example, FIG. 2 illustrates a first LOR 202 that passes through an ROI 204 that includes the heart 206 and a second LOR 208 that does not pass through the ROI. Note that the spatial truncator 138 may be omitted, particularly in cases where a portion of the object is located outside the transverse FOV of the PET imaging system 102, in which case the acquired projection data is spatially truncated.

Returning now to FIG. 1, in the case of a system that includes motion compensation, a local motion compensator 142 compensates for a motion of the ROI. Motion of the object may be measured using a suitable motion monitor such as a respiratory, cardiac, or other physiological monitor in the case of a human patient. Motion may also be detected via an analysis of the projection space or the image space data. Similarly, the motion compensation may be applied to the spatially truncated projection data prior to reconstruction or in the image space domain following reconstruction. Examples of local motion detection and compensation techniques are also described in Patent Application Number PCT/US2007/61597 filed on Feb. 5, 2007 and entitled Local Motion Compensation Based on List Mode Data, and U.S. Provisional Application No. 60/888,560 filed on Feb. 7, 2007 and entitled Motion Estimation in Treatment Planning, both of which applications are commonly owned with the present application and are expressly incorporated by reference herein in their entireties.

A reconstructor 144 uses an iterative reconstruction technique to generate image space data indicative of the distribution of the radionuclide in the object 118. As will be described in greater detail below, the reconstructor 144 includes a local ROI reconstructor 146 that reconstructs the truncated projection data. The reconstructor 144 may also use non-truncated projection data (i.e., projection data that includes those events detected along LORs that do not pass through the ROI) to reconstruct the larger object.

The system may also include an image combiner 148. In such a case, a combined reconstructed image of the larger object (e.g., image(s) acquired by one or both of the CT scanner 104 or the PET portion 102) may be merged or integrated with the image of the local ROI. Where the images are characterized by different coordinate systems, spatial resolutions, or the like, a registration processor may be used to register the images or provide other requisite corrections. Use of an image combiner 148 is particularly useful in local motion compensation or other applications in which it is beneficial to present the ROI in the context of the larger object.

A workstation computer serves an operator console 128. The console 128 includes a human readable output device such as a monitor or display and input devices such as a keyboard and mouse. Software resident on the console 128 allows the operator to perform functions such as interacting with the ROI identifier 140 and the image combiner 148, viewing or otherwise manipulating the image data generated by the PET and CT reconstructors 144, 126, establishing desired scan protocols, initiating and terminating scans, and the like.

Variations on the system 100 are also possible. For example, the CT portion of the scanner may be omitted, located remotely from the PET gantry portion 102, or replaced with another imaging device such as a magnetic resonance (MR) scanner. As another example, attenuation or anatomical information may be provided by a transmission source associated with the PET gantry portion 102.

The local ROI reconstructor 146 will now be further described. While the following discussion will focus on a two-dimensional (2D) reconstruction for clarity of explanation, those of ordinary skill of the art will appreciate that the described techniques are equally applicable and may be readily extended to three-dimensional (3D) reconstruction.

Given an emission object f(x,y) with its attenuation coefficient μ(x,y) in a two-dimensional (2D) space, after rotating by an angle $\phi \in [0, \pi)$ counterclockwise, it becomes the $f_\phi(s,t)$ and $\mu_\phi(s,t)$ in detector coordinates. The detector coordinates (s,t) and the object coordinates (x,y) for a given angle φ are related by:

$$\begin{pmatrix} s \\ t \end{pmatrix} = \begin{pmatrix} \cos\varphi & \sin\varphi \\ -\sin\varphi & \cos\varphi \end{pmatrix} \begin{pmatrix} x \\ y \end{pmatrix} \text{ and}$$

$$\begin{pmatrix} x \\ y \end{pmatrix} = \begin{pmatrix} \cos\varphi & -\sin\varphi \\ \sin\varphi & \cos\varphi \end{pmatrix} \begin{pmatrix} s \\ t \end{pmatrix}$$

Equation 1

In PET imaging, the mean of the measured projection data, after removing random and scatter, correcting for detector efficiency variation, and proper interpolation, can be represented as $g^{TOF}$ (s, t, φ) for TOF capability scanner and as g(s,φ) for conventional scanner, as shown below in Equations 2 and 3, respectively:

$$g^{TOF}(s, t, \varphi) = a(s, \varphi) \int_{-\infty}^{\infty} f_\varphi(s, \tau) h^{TOF}(t - \tau) d\tau \quad \text{Equation 2}$$

$$g(s, \varphi) = a(s, \varphi) \int_{-\infty}^{\infty} f_\varphi(s, t) dt \quad \text{Equation 3}$$

where a(s,φ) is the attenuation factor defined as:

$$a(s, \varphi) = \exp\left(-\int_{-\infty}^{\infty} \mu_\varphi(s, t) dt\right) \quad \text{Equation 4}$$

The term $h^{TOF}$ (t) is the TOF convolution kernel, which is often modeled as a Gaussian distribution with known full-width-half-maximum (FWHM) and ±nσ kernel width (σ=FWHM/2.355). Note that by adding all counts along t in TOF projection $g^{TOF}$ (s,t,φ), it becomes the non-TOF projection g(s,φ).

Due to the limited photon-counting statistics in PET, the measured projection data $\tilde{g}^{TOF}$ (s,t,φ) or $\tilde{g}(s,\varphi)$ are usually modeled as a Poisson random process as illustrated in Equations 5 and 6, respectively:

$$\tilde{g}^{TOF}(s,t,\varphi) \sim \text{Poisson}(g^{TOF}(s,t,\varphi)) \quad \text{Equation 5}$$

$$\tilde{g}(s,q,\varphi) \sim \text{Poisson}(g(s,\varphi)) \quad \text{Equation 6}$$

Given Equations 5 and 6, and assuming that the attenuation coefficient μ(x,y) is known, the goal of PET image reconstruction is to reconstruct the emission object f(x,y).

At high counting statistics, the non-TOF 2D projection $g_{\phi_0}(s,t)$ already provides enough information to reconstruct the object with good precision. The TOF 3D projection provides extra information about the emission object. For example, at a particular projection angle $\phi_0$, after correcting for attenuation, $g^{TOF}_{\phi_0}(s,t)$ is simply the emission object blurred along the t dimension, as shown in Equation 2. If the timing resolution is good enough, it is simply an image restoration problem. We can deblur $g^{TOF}_{\phi_0}(s,t)$ along t dimension and rotate the image clockwise $\phi_0$ angle to get the emission object. This local blur kernel may also provide us unique information about the local tomography property of TOF-PET.

In local tomography, assume we are interested in a small or local ROI of the object centered on coordinate $(x_0, y_0)$, denoted as $\epsilon\{x_0, y_0\}$. This local object ROI can be degenerated into a single pixel $(x_0, y_0)$. Using Equation 1, all LORs that pass through the local ROI can be defined as $\epsilon\{s_0(\phi)\}$, where $s_0(\phi) = x_0 \cos\phi + y_0 \sin\phi$. Given the projection in $\epsilon\{s_0(\phi)\}$, the task of local tomography is to reconstruct the object in the local ROI $\epsilon\{x_0, y_0\}$.

Based on Equations 5 and 6, a log-likelihood is formed on the truncated TOF and non-TOF projection data:

$$\log(G = \tilde{g} \mid f) = \sum_{m \in \epsilon\{s_0(\varphi)\}} \left\{ \tilde{g}_m \log\left(\sum_n H_{mn} f_n\right) - \left(\sum_n H_{mn} f_n\right) \right\}. \quad \text{Equation 7}$$

Here a discrete format of the measured projection $\tilde{g}_m$ and emission object $f_n$ is used, where m indicates the discrete (s,t,φ) indexing for TOF and (s,φ) for non-TOF, and n indicates the discrete (x,y) indexing. The $H_{mn}$ is the system matrix, which represents the probability of a photon emitted from the object element n and gets detected at the detector element m. The system matrix includes the attenuation for both TOF and non-TOF, and the Gaussian convolution kernel for TOF.

Equation 7 is very similar to the log-likelihood of non-truncated projection data. However, the projection data is summed on local LORs that pass through the local ROI instead of the complete projections. Note that even though we are only interested in a local ROI of the object, the forward projection is performed on all object elements. Similar to complete projections, the Hessian matrix of the truncated projections' log-likelihood is also globally convex. Thus there exists a unique maximum solution. Now the question is if this solution is exactly the same as the original emission object within the local ROI. It is more likely to get correct ROI object estimate when the local ROI's size is large. For a small local ROI, TOF is more likely to get the correct object ROI estimate than the non-TOF, since the TOF Gaussian kernel has a better localization property than the non-TOF uniform kernel.

To optimize Equation 7, an expectation-maximization (EM) algorithm is used. The update equation can be expressed as follows, where k is the iteration number:

$$\hat{f}_n^{k+1} = \frac{\hat{f}_n^k}{\sum_{m \in \epsilon\{s_0(\varphi)\}} H_{mn}} \left( \sum_{m \in \epsilon\{s_0(\varphi)\}} H_{mn} \frac{\tilde{g}_m}{\sum_n H_{mn} \hat{f}_n^k} \right). \quad \text{Equation 8}$$

To speed up convergence rate, an ordered-subset (OS) method based on φ is used. The object estimate is updated after all the angles within a subset are visited. One iteration is done after all the subsets are visited.

The forward projection is implemented as a rotate-and-convolve operator for TOF and a rotate-and-sum operator for non-TOF. Both are multiplied with the attenuation factor. The backward projection is implemented as a multiplication of the attenuation first, then as a convolve-and-back-rotate operator for TOF, and as a uniform-spread-and-back-rotate operator for non-TOF. The initial estimate of the object is set to be uniform over the whole image field-of-view (FOV).

An error function can be used to evaluate the performance of the ROI reconstructor 146, particularly in conjunction with a phantom or other study in which the emission object is known. A root-mean-square-error (RMSE) function that evaluates the error the object estimate $\hat{f}^k$ to the emission object f in the ROI can be defined as follows:

$$RMSE_{ROI}\left(\hat{f}^k - f\right) = \sqrt{\frac{1}{nROI} \sum_{n \in \varepsilon\{x_0, y_0\}} \left(\hat{f}_n^k - f_n\right)^2}$$ Equation 9 where nROI is the number of pixels in the local ROI.

Figure 3:
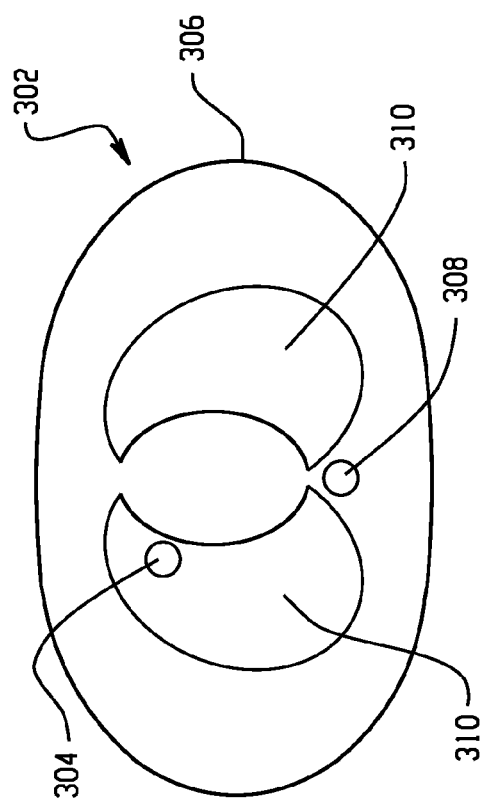
FIG. 3 depict a simulated phantom.

A computer simulation using a 2D 420 millimeter (mm)× 300 mm thorax phantom 302 with a 32 mm diameter lung lesion 304 as depicted generally in FIG. 3 will now be described. The object has 144×144 pixels FOV, 4 mm pixel size.

In the simulated emission object, the lesion 304 to background contrast ratio was set to 8:1, the skin 306 to background ratio was set to 1.3:1, and the bone 308 to background ratio was set to 1.2:1. In the attenuation map, the bone 308 to water ratio was set at 1.2:1; a lung region 310 was simulated as having the attenuation of air.

The projection was simulated with the effect of attenuation, but without any detector efficiency variation, scatter or random. There are 192 samples over π in φ, 144 samples in s with 4 mm pixel size, and 16 samples in t with 36 mm pixel size. The TOF has 700 ps (105 mm) FWHM. A ±5.5σ TOF kernel width is used in projection simulation, and a ±3σ TOF kernel width is used in image reconstruction. In all emission image displays, a linear gray scale with 40% upper threshold is used to show the low contrast detail. A noise-free projection is generated from the thorax phantom, and Poisson noise is added afterwards to simulate noisy projection.

Figure 4:
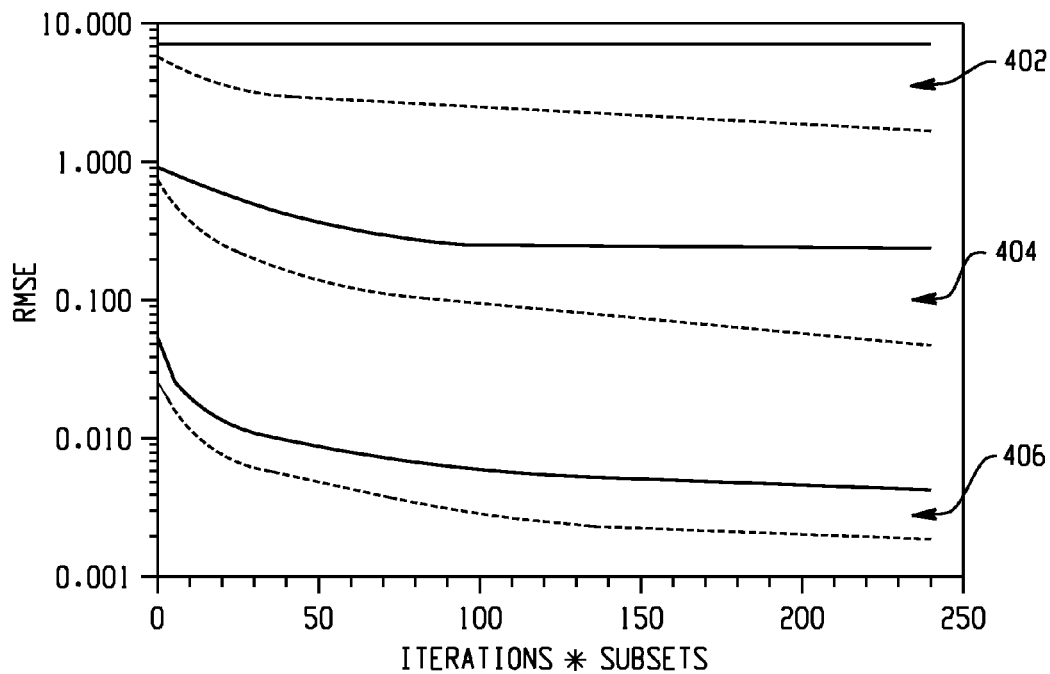
FIG. 4 depicts a root mean square error.

Three sizes of ROI (1 pixel, 36 mm and 144 mm diameter) were selected and centered on the lesion pixel (57, 79). In noise-free projection, the ROI-OS-EM algorithm with 12 subsets and up to 20 iterations are used for both TOF and non-TOF reconstruction. FIG. 4 presents the RMSE of TOF and non-TOF versus number of iterations and subsets for the 1 pixel 402, 36 mm 404, and 144 mm 406 local ROIs respectively, where the dashed lines represent the TOF case and the solid lines represent the non-TOF case, respectively. Both the TOF and non-TOF algorithms converge for medium and large sizes of ROI, but TOF converges closer to the original phantom than the non-TOF. When the ROI is degenerated to 1 pixel, TOF still converge to a solution, though at a lower contrast level, but non-TOF does not converge at all.

Table I displays the maximum and mean absolute bias of TOF and non-TOF ROI at the $10^{th}$ iterations for the three sizes of ROI:

TABLE I

| ROI | TOF MAXBIAS, MEANBIAS | Non-TOF maxBias, meanBias |
|---|---|---|
| 1 pixel | 2.11, 2.11 | 7.37, 7.37 |
| 36 mm | 2.03, 0.436 | 4.89, 1.35 |
| 144 mm | 0.634, 0.0486 | 1.29, 0.118 |

TOF ROI-OS-EM outperforms non-TOF ROI-OS-EM in all cases.

Figure 5:
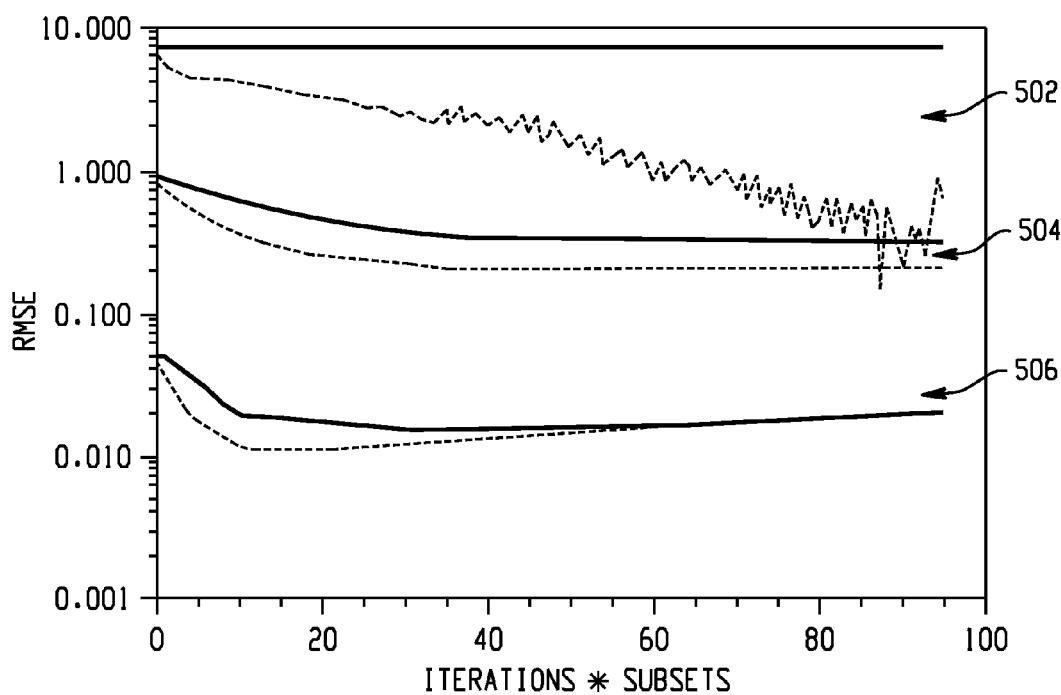
FIG. 5 depicts a root mean square error.

For noisy projections, 400K total counts are generated for both TOF and non-TOF without any truncation. This noise level is similar to the whole body clinical PET after random and scatter are removed. Three sizes of ROI truncated projections (1 pixel, 36 mm and 144 mm centered on lesion) are generated from the noisy complete projections, which has 16K, 62K, and 160K total counts, respectively. FIG. 5 shows the RMSE of TOF and non-TOF versus number of iterations and subsets for the 1 pixel 402, 36 mm 404, and 144 mm 406 local ROIs, where 12 subsets and 8 iterations are used in ROI-OS-EM. The trend is similar to the noise-free case. TOF reaches a smaller ROI RMSE than non-TOF. For the 144 mm ROI 406, at large number of iterations, both TOF and non-TOF's RMSE increases due to the noise amplification, which is very similar to the complete data OS-EM.

For visual comparison, the TOF and non-TOF reconstructions were generated for the 144 mm ROI truncated projection data, and compared with the TOF and non-TOF reconstructions generated from the complete projection data, at 8 subsets and 2 iterations. The TOF and non-TOF reconstructions were combined with the complete data by replacing the object ROI from the complete data with the one from the truncated data. Relative to the non-TOF truncated ROI, the TOF truncated ROI blended better with the complete data image, while non-TOF truncated ROI exhibited noticeable artifacts when combined with the complete data image.

For the large local ROI, TOF ROI-OS-EM reconstructed the region outside the ROI with reasonable accuracy, while the non-TOF ROI-OS-EM reconstruction did not.

While both the TOF and non-TOF reconstructions can provide useful information, performance of the TOF reconstruction was generally superior to that of the non-TOF. For example, the TOF reconstruction has better ROI RMSE than the non-TOF reconstruction in both noise-free and noisy cases. Under the simulation conditions, the TOF reconstruction reconstructed a single pixel ROI, although the non-TOF reconstruction did not. The reconstructed ROI from truncated TOF reconstruction also blended better than the non-TOF into complete data image.

Local tomography, and especially TOF local tomography in the case of a system that provides TOF data, can be used in a number of applications. Examples include patient local motion compensation, where a small ROI image can be generated from the local motion corrected projection data instead of reconstructing the complete dataset. Another example includes the recovery of patient data in cases where portion of the object lies outside the effective FOV of the scanner.

Figure 6:
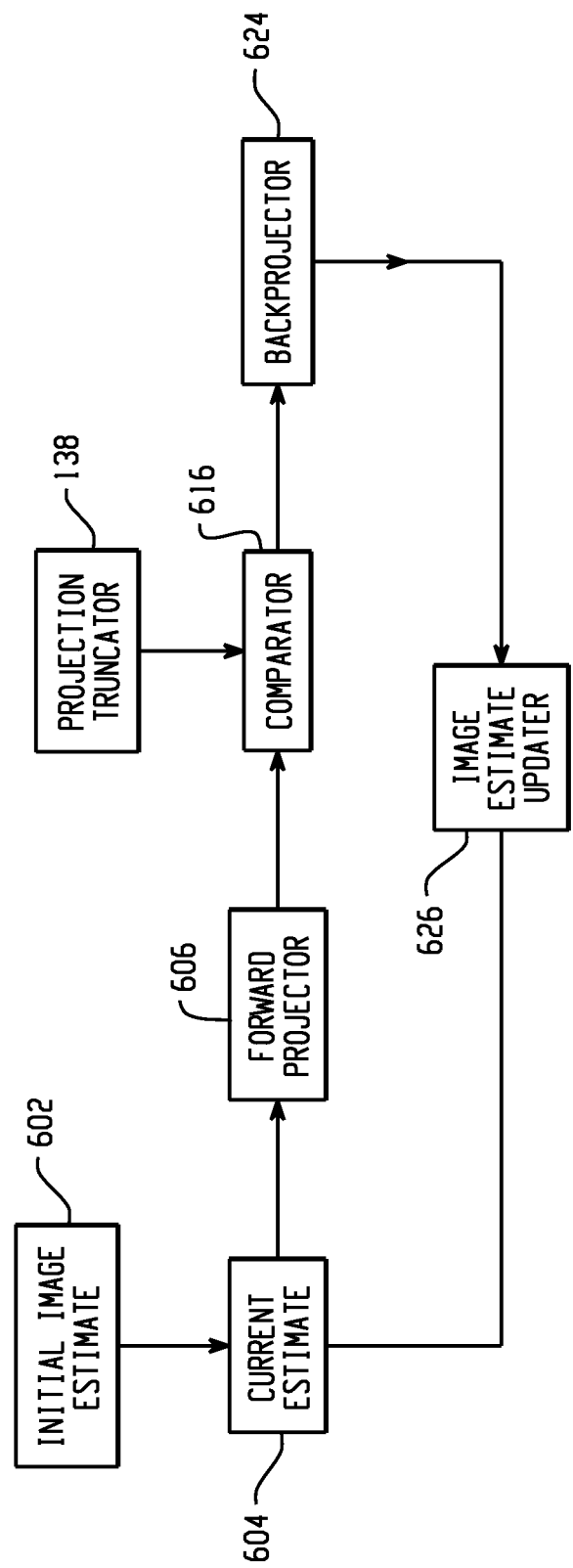
FIG. 6 depicts a local reconstructor.

One implementation of the local reconstructor 146 will now be described with reference to FIG. 6.

An initial object estimate 602 is used to establish an initial current object estimate 604. A forward projector 606 forward projects the current object estimate 604 to produce object estimate projections for those LORs that intersect the ROI. The forward projector 606 may also apply other desired models and/or corrections such as those for detector normalization, attenuation, random and scatter.

A comparator 616 compares the object estimate projections for projection data acquired along LORs that intersect the local ROI and the spatially truncated measured projection data, for example by determining a ratio or difference therebetween.

A backprojector 624 backprojects the compared projections.

An image updater 626 uses the backprojected data to generate a new image estimate. Note that object sensitivity correction is performed using those projections that intersect the ROI.

The updated image estimate becomes the current image estimate and the process is repeated until a termination condition is satisfied, for example to optimize an objective function such as that of EQUATION 7. Note that the optimization is performed over the truncated projections.

Where the reconstructor 146 carries out the reconstruction according to the ordered subsets method, the object estimate is updated once for each subset, and one iteration is completed after each of the subsets is visited.

It should be noted that the reconstruction is not limited to the OS-EM technique and may be performed using other suitable techniques such as ML-EM, RBI-EM or other maximum likelihood methods, RAMLA, CG, or LMQN. Maximum a posterior methods with prior information may also be used. Least squares or other optimization functions may also be used.

Note also that the various functions described above, and particularly those performed by the PET projection truncator 138, the local ROI identifier 140, the motion compensator 142, the reconstructors 144, 146, the image combiner 148, and the registration processor are ordinarily carried out using one or more computer processors. Computer readable instructions that cause the processor(s) to carry out the reconstruction are carried on one or more computer readable media such as computer disks, volatile or non-volatile memory, or the like that are accessible to the processors. The instructions may also be transmitted by way of a suitable communications network such as the internet to storage media accessible to the processors.

Figure 7:
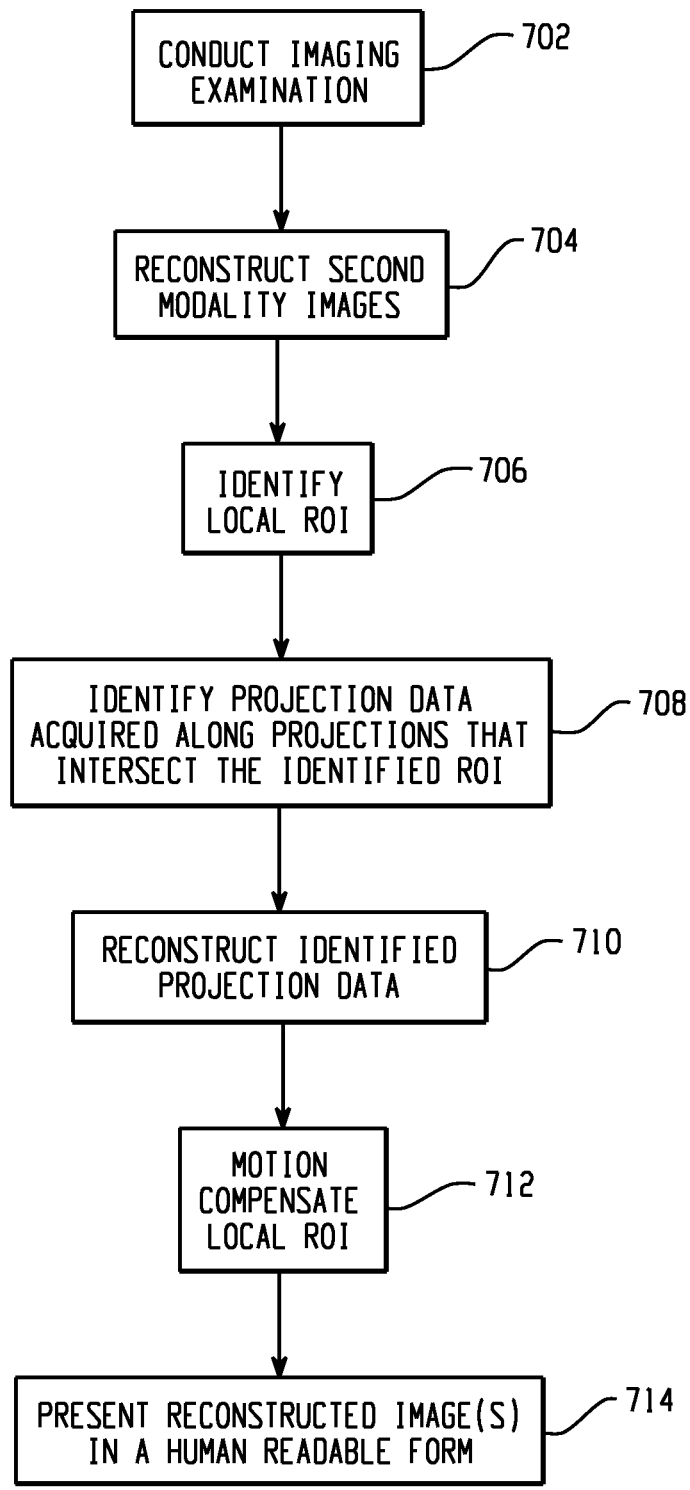
FIG. 7 depicts a method.

Operation will now be further described with reference to FIG. 7.

An imaging examination of the object is conducted at 702. Where the examination is carried out using a combined PET/CT or other hybrid modality scanner, the PET and hybrid modality portions of the examination are ordinarily carried out substantially contemporaneously. It will be appreciated, however, that the scans may be separated in time and/or space. The second modality examination may also be omitted. Note that the further processing of the acquired projection data may be carried out in the absence of the object.

Data from the second modality is reconstructed at 704, for example to produce spatially varying object attenuation data.

The local ROI is identified at 706. Where information from the PET or hybrid portion of the imaging examination is used to identify the local ROI, the relevant projection data should be reconstructed prior to the identification of the ROI.

Projection data acquired along LORs that intersect the identified ROI are identified at 708.

The identified projection data is reconstructed at 710 to generate image space data indicative of the identified ROI and/or the larger object.

Motion compensation of the identified ROI is performed at 712. Where motion compensation is performed in projection space, the motion compensation would ordinarily be performed prior to the reconstruction.

At 714, the reconstructed images are presented in human readable form. If desired, images of the identified ROI may be combined with other image(s) of the object, for example by superimposing or otherwise displaying them in their correct position relative to images produced by one or both of the PET or second modality scans.

It will be understood that the order in which the various steps are performed may be varied as appropriate.

The invention has been described with reference to the preferred embodiments. Of course, modifications and alterations will occur to others upon reading and understanding the preceding description. It is intended that the invention be construed as including all such modifications and alterations insofar as they come within the scope of the appended claims.

What is claimed is:

1. An apparatus comprising:
a projection data spatial truncator that spatially truncates positron emission projection data acquired in a positron emission examination of an object, wherein the projection data spatial truncator (i) selects projection data acquired along lines of response that intersect a region of interest of the object; or (ii) rejects measured projection data acquired lines of response that do not intersect the region of interest;
an iterative reconstructor that reconstructs the truncated projection data to produce first image space data indicative of the object, wherein the truncated projection data consists of projection data acquired along lines of response that intersect a first transverse sub-region of the object, wherein the iterative reconstructor produces second image space data indicative of a second transverse region of the object located outside the first transverse sub-region.

2. The apparatus of claim 1 wherein the acquired projection data includes time of flight data.

3. The apparatus of claim 1 wherein the iterative reconstructor includes:
a forward projector that forward projects an image estimate to produce image estimate projection data for a plurality of lines of response;
a comparator that compares image estimate projection data for lines of response that intersect the region of interest and the truncated projection data;
a backprojector that backprojects the compared projections;
an image estimate updater that uses the backprojected compared projections to update the image estimate.

4. The apparatus of claim 1 including a region of interest identifier that identifies a region of interest of the object and wherein the projection data spatial truncator truncates the spatial projection data as a function of the identified region of interest.

5. The apparatus of claim 4 wherein the region of interest identifier identifies a center of activity.

6. The apparatus of claim 4 wherein the object includes an organ and the region of interest identifier identifies the organ.

7. The apparatus of claim 1 including a motion compensator that compensates for a physiological motion of the object.

8. The apparatus of claim 1 wherein the first image space data includes image space data indicative of a sub-region of the object and the apparatus includes an image combiner that combines the first image data with the second image space data of a region of the object located outside the sub-region to produce a combined image.

9. The apparatus of claim 1 wherein the acquired projection data includes projection data acquired using a time of flight positron emission scanner having a transverse field of view that is smaller than a transverse dimension of the object and the projection truncator identifies projection data acquired along lines of response that intersect the transverse field of view.

10. A positron emission local tomography method comprising:

identifying a region of interest of the object;

spatially truncating the acquired projection data, wherein spatially truncating includes identifying projection data acquired along lines of response that intersect the identified region of interest;

iteratively reconstructing spatially truncated projection data indicative of positron annihilations occurring in an object and acquired using a positron emission scanner to produce first image space data indicative of the object, wherein the spatially truncated projection data consists of projection data acquired along lines of response that intersect a first transverse sub-region of the object;

using the spatially truncated projection data to produce second image space data indicative of a second transverse region of the object located outside the first transverse sub-region; and presenting the first image space data in a human perceptible form.

11. The method of claim 10 wherein the step of identifying a region of interest includes using a processor to identify the region of interest based at least in part on a priori knowledge of the object morphology.

12. The method of claim 10 wherein the step of identifying a region of interest includes identifying a transverse field of view of a second modality scanner used to produce the second image space data indicative of the object.

13. The method of claim 10 wherein iteratively reconstructing includes using the spatially truncated projection data to calculate the value of an objective function.

14. The method of claim 10 including applying a motion compensation to the first image space data.

15. A non-transitory computer readable storage medium containing instructions which, when executed by a computer, cause the computer to carry out a method that comprises:

performing an iterative local reconstruction of spatially truncated projection data acquired in a positron emission examination of an object to produce first image space data indicative of the object, wherein the truncated projection data consists of projection data acquired along lines of response that intersect a first transverse sub-region of the object; and using the truncated data to produce image space data indicative of a second transverse region of the object located outside the first transverse sub-region.

16. The computer readable storage medium of claim 15 wherein the projection data includes time of flight projection data.

17. The computer readable storage medium of claim 15 wherein the projection data includes list mode data.

18. The computer readable storage medium of claim 15 wherein the method includes applying a motion compensation to the truncated projection data.

19. The computer readable storage medium of claim 15 wherein the method includes spatially truncating the projection data.

* * * * *